US008649837B2

(12) United States Patent
Sugo et al.

(10) Patent No.: US 8,649,837 B2
(45) Date of Patent: Feb. 11, 2014

(54) METHOD AND APPARATUS FOR MEASURING PULSE RATE AND OXYGEN SATURATION ACHIEVED DURING EXERCISE

(75) Inventors: Yoshihiro Sugo, Tokyo (JP); Naoki Kobayashi, Tokyo (JP); Sunao Takeda, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 1590 days.

(21) Appl. No.: 12/175,413

(22) Filed: Jul. 17, 2008

(65) Prior Publication Data

US 2009/0024014 A1 Jan. 22, 2009

(30) Foreign Application Priority Data

Jul. 19, 2007 (JP) ................................ 2007-187884

(51) Int. Cl.
*A61B 5/00* (2006.01)

(52) U.S. Cl.
USPC ......................................... 600/323

(58) Field of Classification Search
USPC .................. 600/323, 324, 336, 502
See application file for complete search history.

(56) References Cited

U.S. PATENT DOCUMENTS

| 4,911,167 | A | * | 3/1990 | Corenman et al. ............ 600/324 |
| 5,690,104 | A | | 11/1997 | Kanemoto et al. |
| 7,025,728 | B2 | | 4/2006 | Ito et al. |
| 2004/0267140 | A1 | | 12/2004 | Ito et al. |
| 2007/0049811 | A1 | | 3/2007 | Kobayashi et al. |

FOREIGN PATENT DOCUMENTS

| EP | 1757224 A2 | 2/2007 |
| JP | 3270917 B2 | 4/2002 |
| JP | 2005-95581 A | 4/2005 |
| JP | 2003-135434 A | 5/2005 |
| JP | 2005-245574 A | 9/2005 |
| JP | 2007-83021 A | 4/2007 |

* cited by examiner

*Primary Examiner* — Max Hindenburg
*Assistant Examiner* — Jonathan M Foreman
(74) *Attorney, Agent, or Firm* — Kenealy Vaidya LLP (57) ABSTRACT

In order to measure a pulse rate and an oxygen saturation of a subject who is in an exercised state, each of two pulse wave signals obtained from the subject is separated into a signal component and a noise component. A frequency spectrum of the signal component and a frequency spectrum of the noise component are obtained. It is judged whether a body motion of the subject is occurred based on the frequency spectrum of the signal component and the frequency spectrum of the noise component. A pulsation frequency is determined based on the judgment as to the body motion. The pulse rate is calculated based on the pulsation frequency. The oxygen saturation is calculated based on a ratio of spectra of the two pulse wave signals corresponding to the pulsation frequency.

7 Claims, 5 Drawing Sheets

FIG. 2

| INTENSITY OF NOISE (BODY MOTION) | PART MAINLY MOVED | | RELATIONSHIP BETWEEN FREQUENCIES OF PULSATION AND NOISE (BODY MOTION) | | |
|---|---|---|---|---|---|
| | | | IDENTICAL | NON-DISTINCT | DISTINCT |
| STRONG | ARTERIAL BLOOD | SIGNAL COMPONENT FREQUENCY SPECTRUM | (1) | (2) | (3) |
| | | NOISE COMPONENT FREQUENCY SPECTRUM | | | |
| | VENOUS BLOOD OR TISSUE | SIGNAL COMPONENT FREQUENCY SPECTRUM | (4) | (5) | (6) |
| | | NOISE COMPONENT FREQUENCY SPECTRUM | | | |
| WEAK | ARTERIAL BLOOD | SIGNAL COMPONENT FREQUENCY SPECTRUM | (7) | (8) | (9) |
| | | NOISE COMPONENT FREQUENCY SPECTRUM | | | |
| | VENOUS BLOOD OR TISSUE | SIGNAL COMPONENT FREQUENCY SPECTRUM | (10) | (11) | (12) |
| | | NOISE COMPONENT FREQUENCY SPECTRUM | | | |

FIG. 3

| PRIORITY LEVEL | FFT PATTERN | CONDITIONS IN FIG. 4 | PULSATION FREQUENCY | PULSE RATE | CASES IN FIG. 2 |
|---|---|---|---|---|---|
| 1 | fS1 fS2 fS3 | S13 | fS1 | PR = fS1×60 | N/A |
| 2 | fS1 fS3 fS2 | S14 | fS1 | PR = fS1×60 | N/A |
| 3 | fS2/2 fN fS1 fN fS2 fS3 | S15 | fS1 | PR = fS1×60 | (5), (6), (8), (9), (11), (12) |
| 4 | fS2/2 fN fS1 fSn fS2 fS3 | S16 | fS1 | PR = fS1×60 | (1), (4), (7), (10) |
| 5 | f fS2/2 fN fSn fS2 fS3 | S17 | fS1 | PR = fS1×60 | (3) |
| 6 | fS2/2 fN fSn fS2 fS3 | S18 | fS2/2 | PR = fS2/2×60 | (2) |

FIG. 5

METHOD AND APPARATUS FOR MEASURING PULSE RATE AND OXYGEN SATURATION ACHIEVED DURING EXERCISE

BACKGROUND

The present invention relates to a pulse oximeter that is suitable to be attached to a living body during exercise for measuring a pulse rate and oxygen saturation ($SpO_2$). The present invention also relates to signal processing applicable to even a case where a pulse cycle and a cycle of noise due to body motion induced by exercise become identical with or similar to each other.

Various methods have already been proposed as a method for separating a signal component and a noise component from two signals measured from a single medium almost simultaneously.

Under these methods, processing pertaining to a frequency domain and processing pertaining to a time domain are usually performed. In medical care, there have been known pulse photometers including an apparatus called a photoelectric sphygmograph for measuring a pulse wave and a pulse rate, an apparatus for measuring oxygen saturation $SpO_2$ as measurement of concentration of a light-absorbing substance included in blood, an apparatus for measuring the concentration of abnormal hemoglobin, such as carbon monoxide hemoglobin, Met hemoglobin, an apparatus for measuring the concentration of injected pigment, and the like. Especially, the apparatus for measuring oxygen saturation $SpO_2$ is called a pulse oximeter.

The principle in the pulse photometer includes determining the concentration of a target substance from a pulse wave data signal that is obtained by causing a tissue of a living body to reflect or allow transmission of light of a plurality of wavelengths, which exhibit different absorbing characteristic with respect to the target substance, and continually measuring intensities of transmitted or reflected light.

When noise is mixed into the pulse wave data, a correct concentration cannot be calculated, which will incur the risk of erroneous treatment. In the conventional pulse photometer, in order to reduce noise, there has hitherto been put forward a method for dividing a frequency band thereby determining a correlation between two signals contained in each of the divided frequency bands.

Japanese Patent No. 3270917 discloses a method for plotting two pulse wave signals, which are determined from transmitted light by irradiating a tissue of a living body with light of two different wavelengths, with the amplitude of one pulse wave signal being taken as a vertical axis and the amplitude of the other pulse wave signal being taken as a horizontal axis; determining a regression line of the signals; and determining oxygen saturation of arterial blood and concentration of a light-absorbing substance from the gradient of the regression line.

With this configuration, enhanced precision of measurement and a reduction in power consumption can be attained. However, large amounts of calculations are still required in order to determine a regression line and the gradient of the regression line through use of large amounts of sampling data pertaining to pulse wave signals of respective wavelengths.

Japanese Patent Publication No. 2003-135434A proposes a method that uses frequency analysis but includes determining a fundamental frequency of a pulse wave signal and further filtering the pulse wave signal by use of a filter employing a harmonic frequency of the fundamental frequency in order to enhance precision rather than extracting a pulse wave signal as in the conventional frequency analysis.

Japanese Patent Publication Nos. 2005-95581A and 2005-245574A propose methods for separating noise from a signal by use of a signal separation technique.

However, when noise due to the body motion of a subject, which is ten times as large as a pulse wave in terms of an amplitude ratio, is mixed, all of the above methods encounter difficulty in calculating a pulse rate and oxygen saturation of arterial blood, and further improvements have been desired.

Japanese Patent Publication No. 2007-83021A proposes, as an example of the improvements, a signal processing method in which there is lessened load on calculation processing for extracting a common signal component by processing two signals of the same type which are almost simultaneously measured from a single medium.

However, even in the case of the techniques described in the above publications, when the frequency of noise due to the body motion, such as exercise of a subject, becomes identical with or similar to the pulsation frequency and when the amplitude of noise is large, a pulse rate cannot be measured accurately.

SUMMARY

It is an object of the invention to provide a method and an apparatus for measuring a pulse rate and oxygen saturation, in which a noise component is separated from a signal component in each of two signals which are almost simultaneously measured from a medium; frequency spectra of the respective components are obtained; a frequency, which is to be employed for calculation of a pulse rate, is determined from a relationship between the thus-obtained frequency spectra of the signal component and the noise component and a relationship between peak frequencies of each harmonic wave and peak frequencies of the fundamental wave, thereby calculating a pulse rate; and oxygen saturation ($SpO_2$) is also calculated with the determined frequency.

According to one aspect of the invention, there is provided a method of measuring a pulse rate and an oxygen saturation of a subject who is in an exercised state, comprising:

separating each of two pulse wave signals obtained from the subject into a signal component and a noise component;

obtaining a frequency spectrum of the signal component and a frequency spectrum of the noise component;

judging whether a body motion of the subject is occurred based on the frequency spectrum of the signal component and the frequency spectrum of the noise component;

determining a pulsation frequency based on the judgment as to the body motion;

calculating the pulse rate based on the pulsation frequency; and calculating the oxygen saturation based on a ratio of spectra of the two pulse wave signals corresponding to the pulsation frequency.

There may be configured that the pulsation frequency is determined as a fundamental frequency of the signal component, when it is judged that the body motion is not occurred.

The method may further comprise judging whether a first difference between a first frequency at which the frequency spectrum of the signal component has a maximum amplitude and a second frequency at which the frequency spectrum of the noise component has a maximum amplitude is no less than a first prescribed value, when it is judged that the body motion is occurred. Here, the pulsation frequency is determined as the first frequency when it is judged that the first difference is no less than the first prescribed value.

The method may further comprise judging whether a second difference between the first frequency and one half of a third frequency which is higher than the first frequency and at which the frequency spectrum of the signal component has a peak is less than a second prescribed value, when it is judged that the first difference is less than the first prescribed value. Here, the pulsation frequency is determined as the first frequency when it is judged that the second difference is less than the second prescribed value.

The method may further comprise judging whether a third difference between the one half of the third frequency and a fourth frequency at which the frequency spectrum of the signal component has a second-maximum amplitude is less than a third prescribed value, when the it is judged that the second difference is no less than the second prescribed value. Here, the pulsation frequency is determined as the fourth frequency when it is judged that the third difference is less than the third prescribed value.

The method may further comprise judging whether a ratio of a previously-determined pulsation frequency to a fourth difference between the previously-determined pulsation frequency and the one half of the third frequency is less than a fourth prescribed value, when it is judged that the third difference is no less than the third prescribed value. Here, the pulsation frequency is determined as the one half of the third frequency when it is judged that the ratio is less than the fourth prescribed value.

According to one aspect of the invention, there is provided an apparatus configured to measure a pulse rate and an oxygen saturation of a subject who is in an exercised state, comprising:

a separator, configured to separate each of two pulse wave signals obtained from the subject into a signal component and a noise component;

a spectra obtainer, configured to obtain a frequency spectrum of the signal component and a frequency spectrum of the noise component;

a judge, configured to judge whether a body motion of the subject is occurred based on the frequency spectrum of the signal component and the frequency spectrum of the noise component;

a pulsation frequency determinant, configured to determine a pulsation frequency based on the judgment as to the body motion;

a pulse rate calculator, configured to calculate the pulse rate based on the pulsation frequency; and an oxygen saturation calculator, configured to calculate the oxygen saturation based on a ratio of spectra of the two pulse wave signals corresponding to the pulsation frequency.

According to the invention, influence of noise due to the body motion occurred during exercise is eliminated, thereby enabling measurement of an accurate pulse rate.

When there is motion of venous blood or a tissue other than arterial blood due to the body motion occurred during the exercise of the subject, a signal of a frequency band influenced by the body motion is not used. Hence, accurate measurement of oxygen saturation becomes feasible.

When the subject is in a rest state where no exercise is performed, a conventional method (apparatus), such as a zero-crossing method, that enables measurement of pulsation with high temporal resolution can be selectively used in combination. In that case, there can be obtained temporal resolution sufficient for measurement performed during the subject being at rest in which a pulse rate is low. There is obtained sufficient temporal resolution required to measure fluctuations in a pulse rate for examination of an autonomic nerve.

DETAILED DESCRIPTION OF EXEMPLIFIED EMBODIMENTS

Exemplified embodiments of the invention will be described below in detail with reference to the accompanying drawings.

Figure 1:
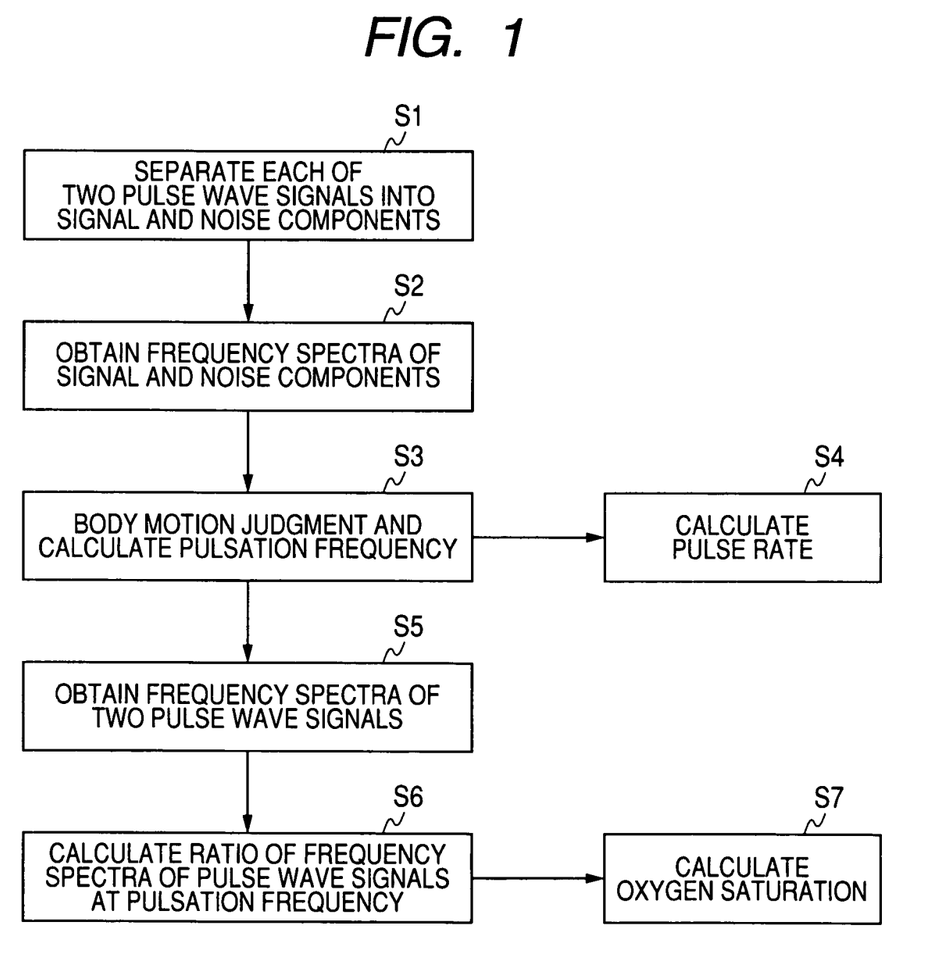
FIG. 1 is a flowchart showing processing performed in a method and an apparatus of the invention.

An overall configuration of data processing performed in a method and an apparatus for measuring a pulse rate and oxygen saturation according to the invention will be described with reference to a processing flowchart shown in FIG. 1.

Each of two signals (IR, R) of the same type which are almost simultaneously measured from a single medium are separated into a signal component and a noise component (step S1).

Frequency spectra of a signal component and a noise component separated in step S1 are obtained by FFT processing or the like (step S2).

A pulsation frequency is calculated by a determination as to whether or not there is body motion and the method which is described later in detail (step S3).

A pulse rate is calculated based on the pulsation frequency obtained in step S3 (step S4).

Frequency spectra of the signals R and IR at the pulsation frequency obtained in step S3 are calculated (step S5).

A ratio between the frequency spectra of R and IR at the pulsation frequency obtained in step S5 is calculated (step S6).

Oxygen saturation ($SpO_2$) is calculated from the ratio between the spectrum of R and the spectrum of IR obtained in step S6.

A pulsation frequency of the present invention is rendered according to the following characteristics.

In addition to a fundamental wave, the spectra at the pulsation frequency measured from the medium include a second harmonic wave, a third harmonic wave, and the like. The second harmonic wave, the third harmonic wave, and the like, appear at integral multiples of the fundamental wave frequency. In ordinary cases, the amplitudes of the spectra exhibit the property of becoming smaller in sequence of the fundamental wave, the second harmonic wave, the third harmonic wave.

When there is no body motion, arterial blood undergoes pulsation, whereupon a change arises in the thickness of the arterial blood. On the other hand, when there is body motion, changes arise simultaneously in the thickness of arterial blood and venous blood.

The analysis (clarification) according to the present invention is performed on the basis of the following three viewpoints.

(a) Which of arterial blood and venous blood is mainly moved during body motion?

The signal component is generated by the arterial blood. When the arterial blood is mainly moved during body motion, the influence of body motion appears in signal component. When the venous blood is mainly moved during body motion, the influence of body motion appears in a noise component.

(b) Are the frequency of body motion and the pulsation frequency identical with each other, similar to each other, or distinct from each other?

When the frequency of body motion and the pulsation frequency identical with each other or similar to each other, the spectrum of the signal component cannot be separated from the spectrum due to the body motion, and hence a single peak spectrum tends to be obtained.

(c) Is body motion strong or weak?

When body motion is strong, the motion of arterial blood and venous blood becomes large. Hence, the amplitude of spectrum induced by the body motion becomes larger. When body motion is weak, the amplitudes of spectra of body motion become smaller.

Examples in which, after each of signal components and each of noise components are separated from two signals (IR, R) almost simultaneously measured from a medium to be measured (subject body) that is moved, frequency spectra of the components are determined in accordance with the above three viewpoints will be described by reference to FIG. 2.

Figure 2:
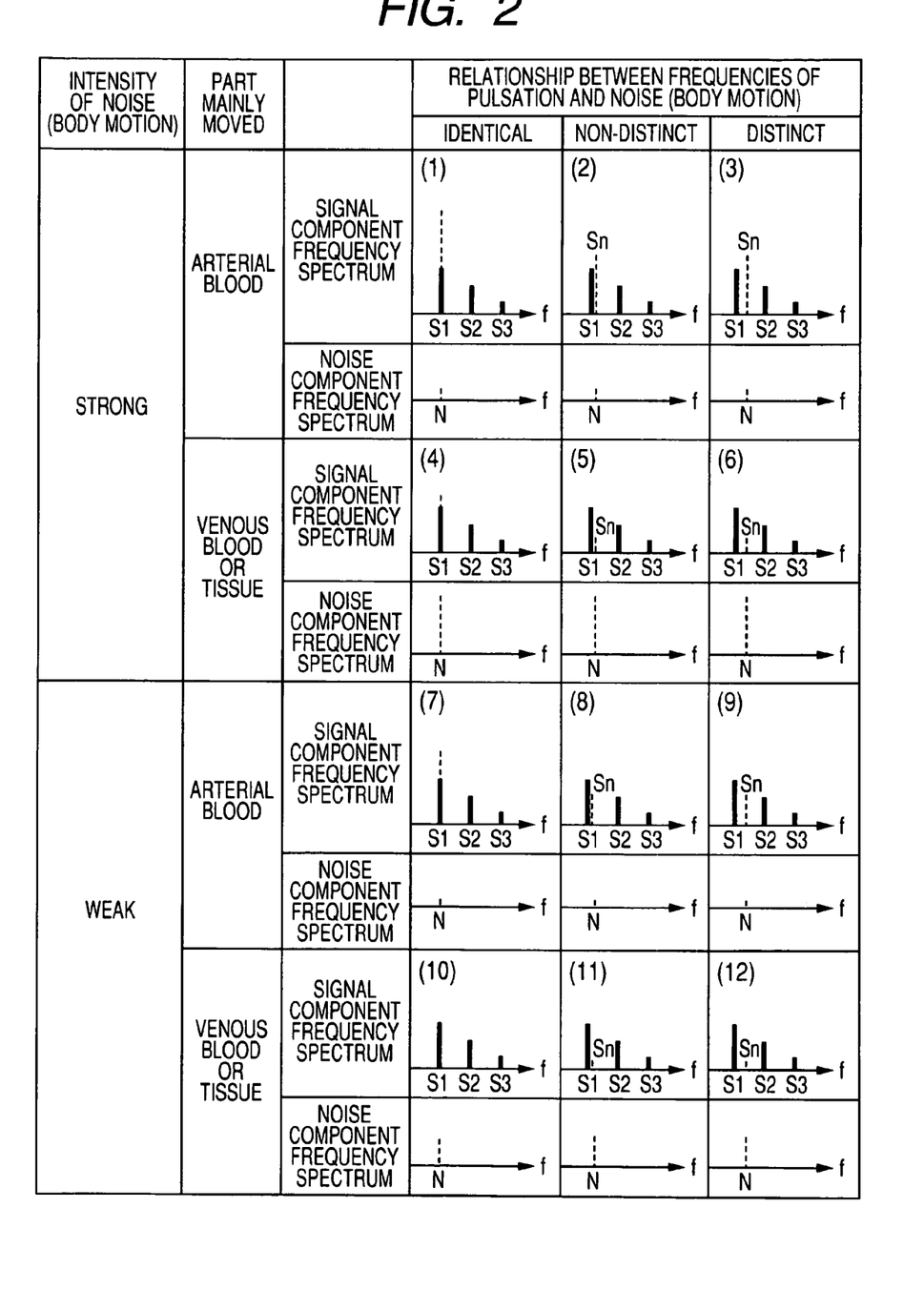
FIG. 2 is a table showing frequency spectra of a signal component and a noise component derived from pulse wave signals of a subject in cases that a body motion of the subject is occurred.

FIG. 2 shows a relationship between the frequency spectrum of the signal component and the frequency spectrum of the noise component obtained when there is body motion. In this figure, a solid line shows the frequency spectrum derived from pulsation, and a dashed line indicates a frequency spectrum derived from body motion.

When two frequency spectra are the same, the signal component cannot be separated from the noise component, and the components are displayed as integrated spectra as shown in (1), (4), (7), and (10) in FIG. 2.

In the case of a frequency spectrum derived from the pulsation and a frequency spectrum derived from the body motion have frequencies S1 and Sn which are almost the same, the spectra cannot be completely separated from each other. Even when the spectra are subjected to FFT processing, a single peak is exhibited. Hence, the frequency S1 per se cannot be identified as shown in (2), (5), (8), and (11) in FIG. 2.

Because both the arterial blood and the venous blood are moved in accordance with the body motion, when the body motion is large, the amplitude of a spectrum due to the body motion becomes greater. In contrast, when body motion is small, the spectrum due to the body motion becomes smaller.

In connection with twelve cases shown in FIG. 2, there is provided the reason why the frequency S1 of the signal component frequency spectrum can be determined to be the pulsation frequency.

In the cases of (6), (9), (12), (5), (8), and (11) shown in FIG. 2, since a signal peak frequency S1 at which the signal component frequency spectrum has a maximum amplitude is different from a noise peak frequency N at which the noise component frequency spectrum has a maximum amplitude, the frequency S1 can be determined to be the pulsation frequency.

In the cases of (1), (4), (7), and (10) shown in FIG. 2, the signal peak frequency S1 and the noise peak frequency N are identical with each other. However, since a frequency peak S2 that is double the frequency S1 is present, the frequency S1 can be determined to be the pulsation frequency.

In the case of (3) in FIG. 2, the signal peak frequency Sn and the noise peak frequency N are almost the same. However, there is no frequency peak that is double the signal peak frequency Sn. Hence, the peak frequency Sn is not derived from the pulsation frequency and can be determined to be the frequency derived from the body motion.

Since the peak is present at the frequency S2 which is double of the signal second-peak frequency S1, the frequency S1 can be determined to be the pulsation frequency.

In the case of (2) in FIG. 2, the signal peak frequency Sn and the noise peak frequency N are almost the same. However, there is no frequency peak that is double the signal peak frequency Sn. Hence, the peak frequency Sn is not derived from the pulsation frequency and can be determined to be the frequency derived from the body motion. However, the frequency S1 cannot be distinguished from the frequency Sn and cannot be identified as the pulsation frequency.

Accordingly, a frequency that is one-half the signal second-peak frequency S2 is compared with the pulsation frequency determined by a previous determination. When a difference (change rate) falls within a prescribed range, the one-half frequency of the signal second-peak frequency S2 can be determined to be the pulsation frequency. Here, the prescribed range is such a change rate (e.g., 10%) that a pulse rate can exhibit the maximum physiologic change between the previous determination and the current determination.

Figure 3:
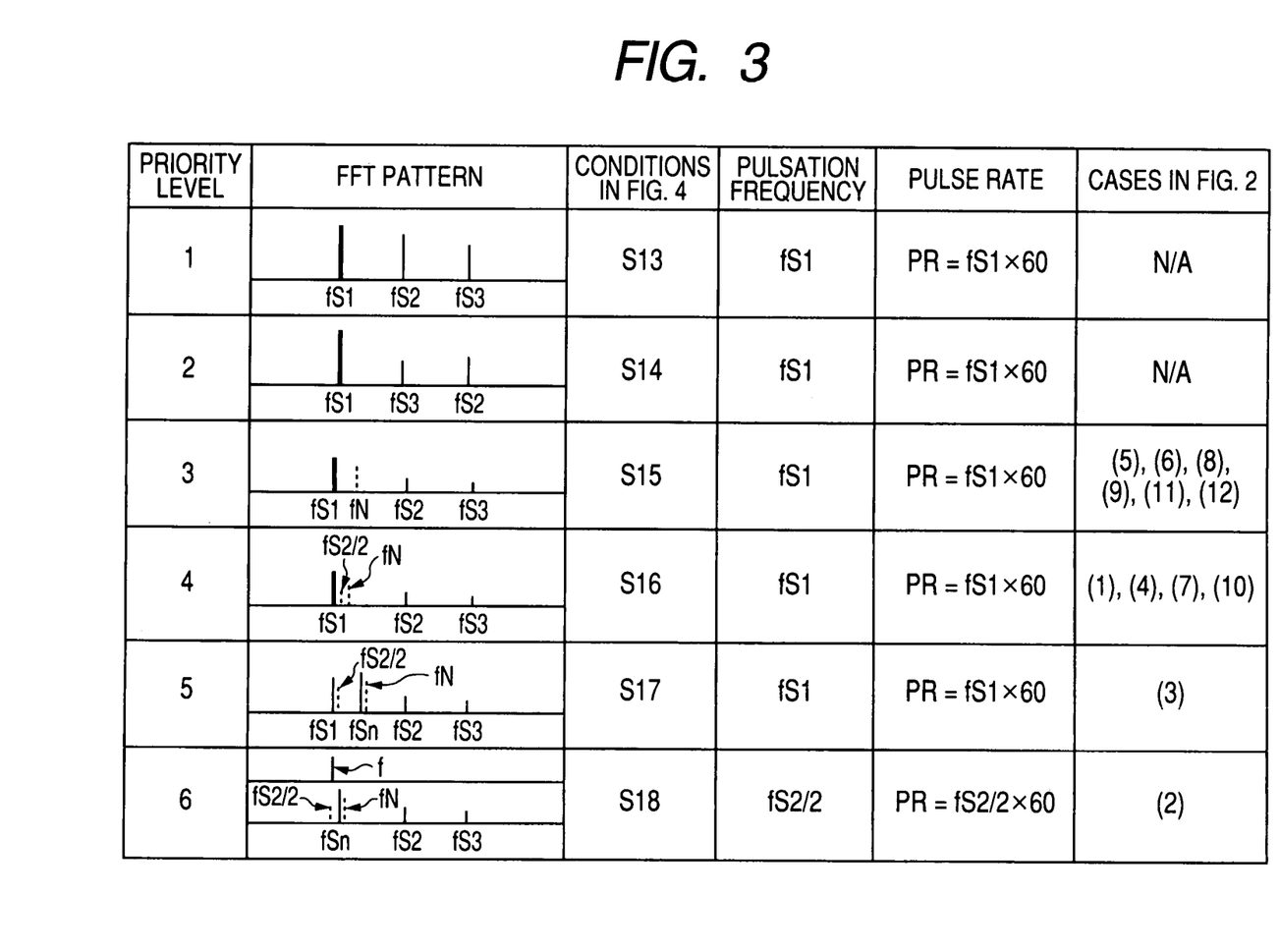
FIG. 3 is a table summarizing judgments for calculating a pulse rate performed in the cases shown in FIG. 2.

The above judgments are summarized in FIG. 3. Since examples labeled with the priority levels 1 and 2, are cases where there is no body motion, they are not included in the cases (1) to (12) shown in FIG. 2.

Detailed procedures for calculating a pulse rate (PR) of the present invention will be described by reference to a flowchart shown in FIG. 4. This processing is referred to as a "method for determining the pulsation frequency with a kinetic algorithm." A determination technique based on the flowchart is suitable for use in automatic determination processing performed by a computer that is incorporated in an apparatus for measuring a pulse rate and oxygen saturation.

Two signals (IR, R) measured simultaneously from a medium to be measured (subject body) are separated into a signal component and a noise component. By FFT processing or the like, frequency spectra of the respective components are determined (step S1).

It is determined whether or not there is an fN (the spectrum of the noise component due to the body motion) (step S12).

When the result of the determination in step S12 is No, fS1, fS2, and fS3, which are frequencies of a signal component spectrum, are integral multiples, and heights of peaks of the frequencies exhibit a relationship of fS1>fS2>fS3. It is also determined whether or not a difference among the heights falls within a range of ±20% (step S13).

A determination performed in step S13 corresponds to an FFT pattern in the case of the priority level 1 in FIG. 3, and peaks of the fundamental wave fS1, the second harmonic wave (fS2), and the third harmonic wave (fS3) satisfy conditions for fS1>fS2>fS3.

When the result of the determination in step S13 is Yes, the fundamental wave fS1 is designated as a pulsation frequency, and a pulse rate (PR) is calculated as PR=60·fS1 (step S19).

When the result of the determination in step S13 is No, fS1, fS2, and fS3, which are frequencies of signal component spectrum, are integral multiples, and peaks of the frequencies exhibit a relationship of fS1>fS3>fS2. It is also determined whether or not a difference among the peaks falls within a range of ±20% (step S14).

A determination performed in step S14 corresponds to an FFT pattern in the case of the priority level 2 in FIG. 3, and peaks of the fundamental wave fS1, the second harmonic wave (fS2), and the third harmonic wave (fS3) satisfy conditions for fS1>fS2>fS3.

When the result of the determination in step S14 is Yes, the fundamental wave fS1 is designated as a pulsation frequency, and a pulse rate (PR) is calculated as PR=60·fS1 (step S19).

When the result of the determination in step S14 is No or the result of the determination in step S12 is Yes, it is determined whether or not a relationship |fS1−fN|≥Δf1 [Hz] is satisfied (step S15). Here, fS1 designates the maximum amplitude peak frequency of the signal component frequency spectrum (signal peak frequency); and fN designates the maximum amplitude peak frequency of the noise component frequency spectrum (noise peak frequency). A value of Δf1 is; for example, 0.25 [Hz].

A determination performed in step S15 corresponds to an FFT pattern in the case of the priority level 3 in FIG. 3, namely, a case where a difference between the frequency fS1 of the signal component S1 of the fundamental wave and the frequency fN of the noise component is a prescribed value (e.g., 0.25 Hz) or more as shown in the cases of (5), (6), (8), (9), (11), and (12) in FIG. 2.

When the result of the determination in step S15 is Yes, fS1 is designated as a pulsation frequency, and a pulse rate (PR) is calculated as PR=60·fS1 (step S19).

When the result of the determination in step S15 is No, it is determined whether or not the relationships |fS1−fN|<Δf1 [Hz] and |fS1−fS2/2|<Δf2 [Hz] are satisfied (step S16). Here, fS2 designates a frequency at which the signal component frequency spectrum has a peak and that is higher than the signal peak frequency fS1. Values of Δf1 and Δf2 are; for example, 0.25 [Hz].

A determination rendered in step S16 corresponds to an FFT pattern in the case of the priority level 4 in FIG. 3, namely, where a difference between the frequency fS1 of the signal component of the fundamental wave and the frequency fN of the noise component is less than a prescribed value (e.g., 0.25 Hz) and a difference between the signal peak frequency fS1 and a one-half frequency of the frequency fS2 of the second harmonic wave S2 is less than a prescribed value (e.g., 0.25 Hz) as in the cases of (1), (4), (7), and (10) in FIG. 2.

When the result of the determination in step S16 is Yes, fS1 is designated as a pulsation frequency, and a pulse rate (PR) is calculated as PR=60·fS1 (step S19).

When the result of the determination in step S16 is No, it is determined whether or not the following relationships are satisfied (step S17). Here, fSn designates the maximum amplitude signal peak frequency; fN designates the maximum amplitude peak frequency of the noise component frequency spectrum; fS1 designates a frequency at which the signal component frequency spectrum has a second peak; fS2 designates a frequency at which the signal component frequency spectrum has a peak and that is higher than the frequency fS1; and fS3 designates a frequency at which the signal component frequency spectrum has a peak and that is higher than the frequency fS2.

|fSn−fN|<Δf1 [Hz];
|fSn−fS2/2|≥Δf2 [Hz];
|fSn−fS3/2|≥Δf2 [Hz]; and
|fS1−fS2/2|<Δf2 [Hz]

A determination performed in step S17 corresponds to an FFT pattern in the case of the priority level 5 in FIG. 3, namely, a case where a difference between the frequency fSn of the noise (body motion) Sn appearing in the signal component frequency spectrum in the case (3) in FIG. 2 and the frequency fN of the noise component N is less than a prescribed value (e.g., 0.25 Hz), and where a difference between the frequency fSn and a one-half of the frequency fS2 of the signal component of the second harmonic wave S2 is a prescribed value (e.g., 0.25 Hz) or more.

Moreover, the determination corresponds to a case where a difference between the frequency fSn and a one-half of the frequency fS3 of the signal component of the third harmonic wave S3 is a prescribed value (e.g., 0.25 Hz) or more, and where a difference between the frequency fS1 of the signal component S1 of the fundamental waveform and the one-half of the frequency fS2 is less than a prescribed value (e.g., 0.25 Hz).

When the result of the determination in step S17 is Yes, fS1 is designated as a pulsation frequency, and a pulse rate (PR) is calculated as PR=60·fS1 (step S19).

When the result of the determination in step S17 is No, it is determined whether or not the following relationships are satisfied (step S18). Here, "f" designates a pulsation frequency obtained in the previous determination. A prescribed value "r" is, for example, 10%.

|fSn−fN|<Δf1 [Hz];
|fSn−fS2/2|≥Δf2 [Hz];
|fSn−fS3/2|<Δf2 [Hz];
|fS2/2−f|/f<r [%]

A determination performed in step S18 corresponds to an FFT pattern in the case of the priority level 6 in FIG. 3, namely, a case where a difference between the frequency fSn of the noise (body motion) Sn appearing in the signal component frequency spectrum in the case of (2) in FIG. 2 and the frequency fN of the noise component N is less than a prescribed value (e.g., 0.25 Hz), and where a difference between the frequency fSn and a one-half of the frequency fS2 of the signal component of the second harmonic wave S2 is a prescribed value (e.g., 0.25 Hz) or more.

Moreover, the determination corresponds to a case where a difference between the frequency fSn and a one-half frequency of the frequency fS3 of the signal component of the third harmonic wave S3 is a prescribed value (e.g., 0.25 Hz) or more, and where a ratio of the previous pulsation frequency "f" to a difference between the one-half of the frequency fS2 and the previous pulsation frequency "f" is less than a prescribed value (e.g., 10%).

When the result of the determination in step S18 is Yes, fS2/2 is designated as a pulsation frequency, and a pulse rate (PR) is calculated as PR=60·fS2/2 (step S20).

When the result of the determination in step S18 is No, a pulsation frequency is not determined, and processing returns to step S12.

Figure 4:
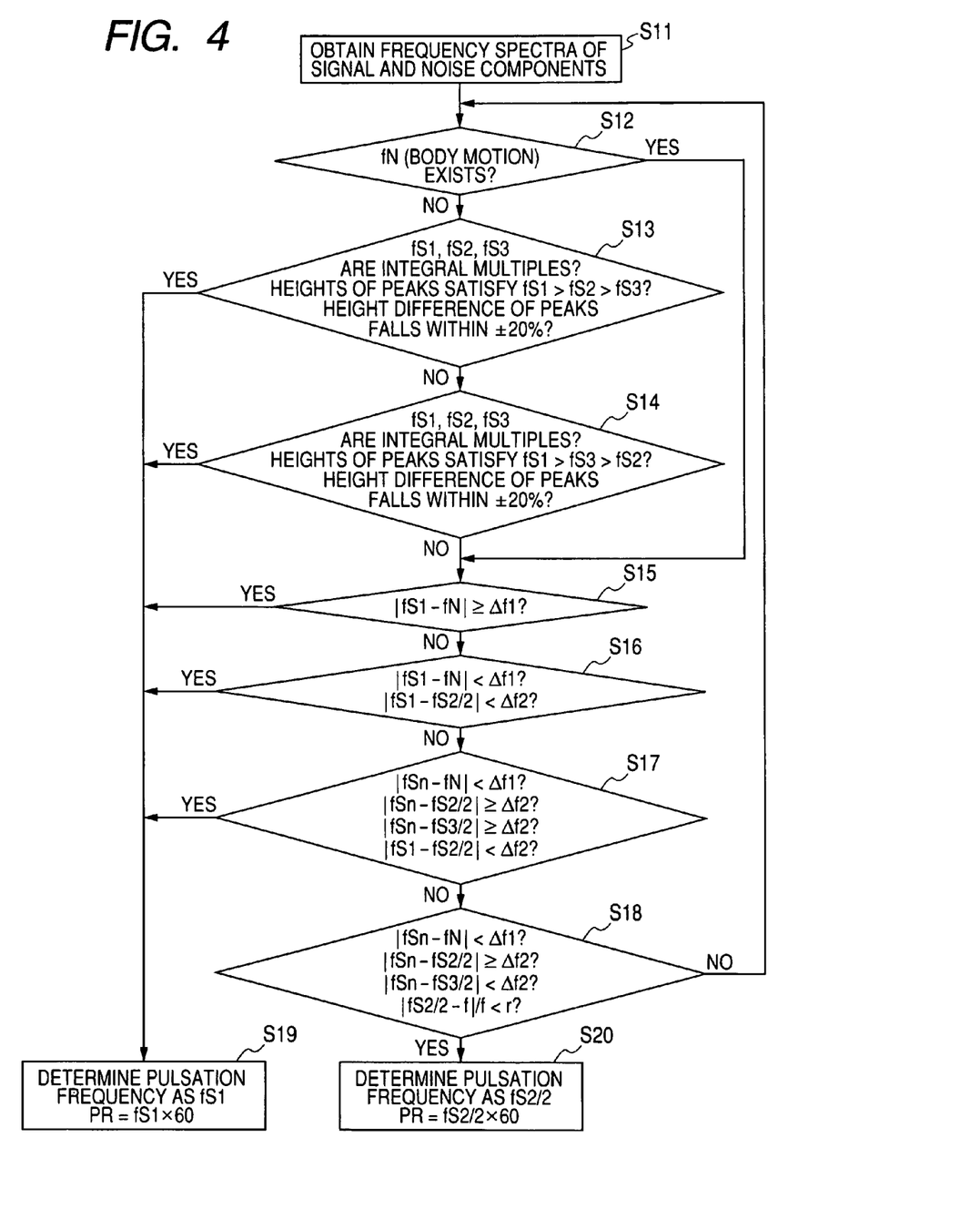
FIG. 4 is a flow chart showing detailed processing for calculating the pulse rate.

The flowchart shown in FIG. 4 shows processes up to calculation of a pulse rate. However, oxygen saturation (SpO$_2$) is obtained by calculating a ratio between the two signals (IR, R) that have been almost simultaneously measured from a medium at the pulsation frequency used for calculating a pulse rate.

Figure 5:
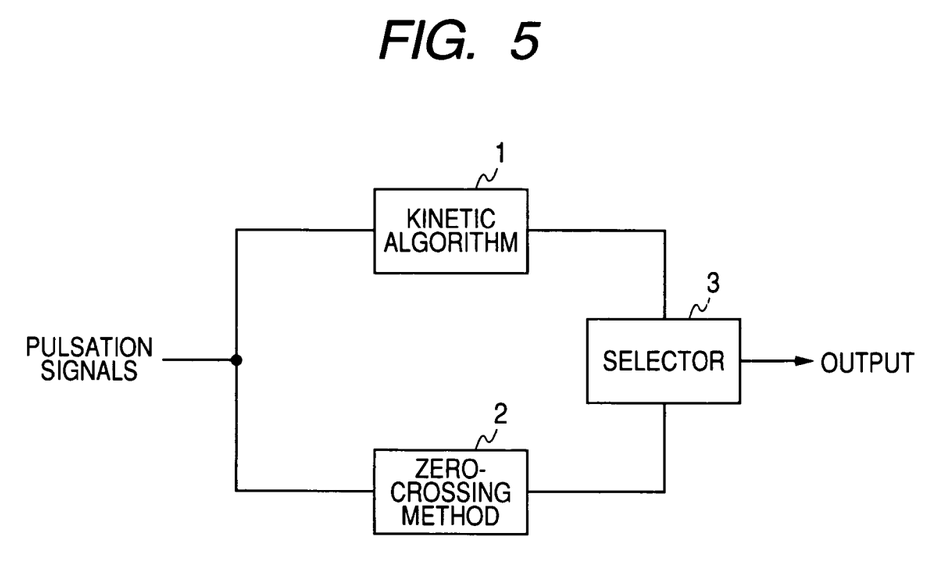
FIG. 5 is a block diagram showing a system in which a measurement apparatus configured to execute a kinetic algorism and a measurement apparatus configured to execute a zero-crossing method are used in combination.

FIG. 5 shows an example in which the "method for determining a pulsation frequency with a kinetic algorithm" of the present invention and calculation of a pulse rate under the conventional "zero-crossing method" are used in combination.

In FIG. 5, a measurement apparatus 1 operable to perform the "method for determining a pulsation frequency determined by a kinetic algorithm" and a measurement apparatus 2 operable to perform the "zero-crossing method" are used in combination. A selector 3 is configured to select an output from the measurement apparatus 1 when body motion is detected, and an output from the measurement apparatus 2 when body motion is not detected.

With the above configuration, when motion of a tissue other than arterial blood or motion of venous blood due to the body motion is detected, a signal of frequency band derived from the body motion is not used. Hence, accurate measurement of oxygen saturation can be attained. On the other hand, when body motion is not detected, the conventional measurement method (apparatus) that enables measurement of pulsation with high temporal resolution, such as a zero-crossing method, can be selectively used. In such a case, temporal resolution sufficient for performing measurement during a resting period where a pulse rate is low is acquired. Moreover, temporal resolution required to measure fluctuations in pulse rate for examination of an autonomic nerve is acquired.

Although only some exemplary embodiments of the invention have been described in detail above, those skilled in the art will readily appreciated that many modifications are possible in the exemplary embodiments without materially departing from the novel teachings and advantages of the invention. Accordingly, all such modifications are intended to be included within the scope of the invention.

The disclosure of Japanese Patent Application No. 2007-187884 filed Jul. 19, 2007 including specification, drawings and claims is incorporated herein by reference in its entirety.

What is claimed is:

1. A method of measuring a pulse rate and an oxygen saturation of a subject who is in an exercised state, comprising:
    separating each of two pulse wave signals obtained from the subject into a signal component and a noise component;
    obtaining a frequency spectrum of the signal component and a frequency spectrum of the noise component;
    judging whether a body motion of the subject is occurred based on the frequency spectrum of the signal component and the frequency spectrum of the noise component;
    determining a pulsation frequency based on the judgment as to the body motion;
    calculating the pulse rate based on the pulsation frequency; and
    calculating the oxygen saturation based on a ratio of spectra of the two pulse wave signals corresponding to the pulsation frequency.

2. The method as set forth in claim 1, wherein:
    the pulsation frequency is determined as a fundamental frequency of the signal component, when it is judged that the body motion is not occurred.

3. The method as set forth in claim 1, further comprising:
    judging whether a first difference between a first frequency at which the frequency spectrum of the signal component has a maximum amplitude and a second frequency at which the frequency spectrum of the noise component has a maximum amplitude is no less than a first prescribed value, when it is judged that the body motion is occurred, wherein:
    the pulsation frequency is determined as the first frequency when it is judged that the first difference is no less than the first prescribed value.

4. The method as set forth in claim 3, further comprising:
    judging whether a second difference between the first frequency and one half of a third frequency which is higher than the first frequency and at which the frequency spectrum of the signal component has a peak is less than a second prescribed value, when it is judged that the first difference is less than the first prescribed value, wherein:
    the pulsation frequency is determined as the first frequency when it is judged that the second difference is less than the second prescribed value.

5. The method as set forth in claim 4, further comprising:
    judging whether a third difference between the one half of the third frequency and a fourth frequency at which the frequency spectrum of the signal component has a second-maximum amplitude is less than a third prescribed value, when the it is judged that the second difference is no less than the second prescribed value, wherein:
    the pulsation frequency is determined as the fourth frequency when it is judged that the third difference is less than the third prescribed value.

6. The method as set forth in claim 5, further comprising:
    judging whether a ratio of a previously-determined pulsation frequency to a fourth difference between the previously-determined pulsation frequency and the one half of the third frequency is less than a fourth prescribed value, when it is judged that the third difference is no less than the third prescribed value, wherein:
    the pulsation frequency is determined as the one half of the third frequency when it is judged that the ratio is less than the fourth prescribed value.

7. An apparatus configured to measure a pulse rate and an oxygen saturation of a subject who is in an exercised state, comprising:
    a separator, configured to separate each of two pulse wave signals obtained from the subject into a signal component and a noise component;
    a spectra obtainer, configured to obtain a frequency spectrum of the signal component and a frequency spectrum of the noise component;
    a judge, configured to judge whether a body motion of the subject is occurred based on the frequency spectrum of the signal component and the frequency spectrum of the noise component;
    a pulsation frequency determinant, configured to determine a pulsation frequency based on the judgment as to the body motion;
    a pulse rate calculator, configured to calculate the pulse rate based on the pulsation frequency; and
    an oxygen saturation calculator, configured to calculate the oxygen saturation based on a ratio of spectra of the two pulse wave signals corresponding to the pulsation frequency.

* * * * *